US00PP09232P

United States Patent [19]

Svejda

[11] Patent Number: Plant 9,232

[45] Date of Patent: Aug. 8, 1995

[54] SHRUB ROSE PLANT NAMED 'CAPTAIN SAMUEL HOLLAND'

[75] Inventor: Felicitas J. Svejda, Nepean, Canada

[73] Assignee: Her Majesty the Queen in right of Canada, as represented by the Minister of Agriculture, Ottawa, Canada

[21] Appl. No.: 215,824

[22] Filed: Mar. 22, 1994

[51] Int. Cl.[6] ..... A01H 5/00

[52] U.S. Cl. ..... Plt./1

[58] Field of Search ..... Plt. 1, 22, 27, 28

[56] References Cited

PUBLICATIONS

Ogilvie, et al., 1991, "'Captain Samuel Holland' Rose", Hortscience 26(10):1344–1345.

*Primary Examiner*—Howard J. Locker

*Attorney, Agent, or Firm*—Burns, Doane, Swecker & Mathis.

[57] ABSTRACT

A new and distinct variety of shrub rose plant is provided which forms on an intermediate basis attractive fuchsia red blossoms that commonly are borne in clusters. The new variety exhibits a spreading and trailing growth habit with glossy foliage, and good winter hardiness. Resistance to powdery mildew and blackspot has been observed. The new variety progpagates well by the use of softwood stem cuttings, and is well adapted for growing as colorful ornamentation in the landscape.

4 Drawing Sheets

SUMMARY OF THE INVENTION

The new variety of shrub rose plant of the present invention was created by artificial pollination during 1981 at the Central Experimental Farm, Ottawa, Ontario, Canada. The female parent (i.e., the seed parent) was *Rosa kordesii*×(Red Dawn×Suzanne), and the male parent (i.e., the pollen parent) was [(*Rosa kordesii*×(Red Dawn×Suzanne)×(Red Dawn-×Suzanne)]. Each of the named plants utilized in the breeding program was non-patented in the United States. Selective study carried out at Ottawa, Ontario, Canada, resulted in the identification of a single plant of the new variety.

It was found that the new variety of shrub rose plant of the present invention possesses the following combination of characteristics:

(a) exhibits a spreading and trailing growth habit with glossy foliage,
(b) forms in clusters attractive fuchsia red blossoms,
(c) propagates well by the use of softwood cuttings,
(d) exhibits a good winter hardiness, and
(e) is particularly well suited for growing in the landscape.

The rose plants can be grown well on their own roots out-of-doors without protection at L'Assomption, Quebec, Canada. The blossoms commonly appear on an intermediate basis. Resistance to powdery mildew and blackspot is exhibited.

The new variety well meets the needs of the horticultural industry. It can be grown to advantage as attractive ornamentation in parks, gardens, public areas, and residential landscapes. It is particularly well suited for growing in the landscape.

The characteristics of the new variety have been found to be homogenous and stable and have been shown to be strictly transmissible by asexual propagation by the rooting of softwood stem cuttings and by tissue culture conducted at L'Assomption, Quebec, Canada.

The new variety has been named the Captain Samuel Holland variety.

BRIEF DESCRIPTION OF THE PHOTOGRAPHS

The accompanying photographs show, as nearly true as it is reasonably possible to make the same in color illustrations of this character, typical specimens of plants and plant parts of the new variety. The rose plants of the new variety described herein were approximately 5 to 6 years of age and were photographed during September 1993 while growing on their own roots at L'Assomption, Quebec, Canada.

FIG. 1 illustrates a group of open flowers and foliage of the new variety while growing in the landscape, FIG. 2 illustrates an open flower and buds of the new variety with foliage while growing in the landscape, FIG. 3 illustrates a specimen of a young bud of the new variety wherein the sepals are open and the petals are beginning to open, FIG. 4 illustrates a specimen of a young flower of the new variety wherein the petals are in a more advanced stage of opening, FIG. 5 illustrates a specimen of a young flower of the new variety as the petals assume a further stage of opening, FIG. 6 illustrates a specimen of a flower of the new variety at a more advanced stage of opening than as illustrated in FIG. 5, FIG. 7 illustrates a specimen of a flower of the new variety at a more advanced stage of opening than as illustrated in FIG. 6, FIG. 8 illustrates a specimen of a fully open flower of the new variety, FIG. 9 illustrates on the left a specimen of a floral receptacle showing the arrangement of the stamens (sepals removed), and on the right a specimen of a floral receptacle showing the arrangement of the pistils (sepals and stamens removed), FIG. 10 illustrates a specimen of new growth of the new variety, FIG. 11 illustrates the upper surfaces of typical leaves of the new variety with a specimen having seven leaflets being shown on the left and a specimen having five leaflets being shown on the right, and FIG. 12 illustrates the under surfaces of typical leaves of the new variety with a specimen having seven leaflets being shown on the left and a specimen having five leaflets being shown on the right.

DETAILED DESCRIPTION

Figure 1:
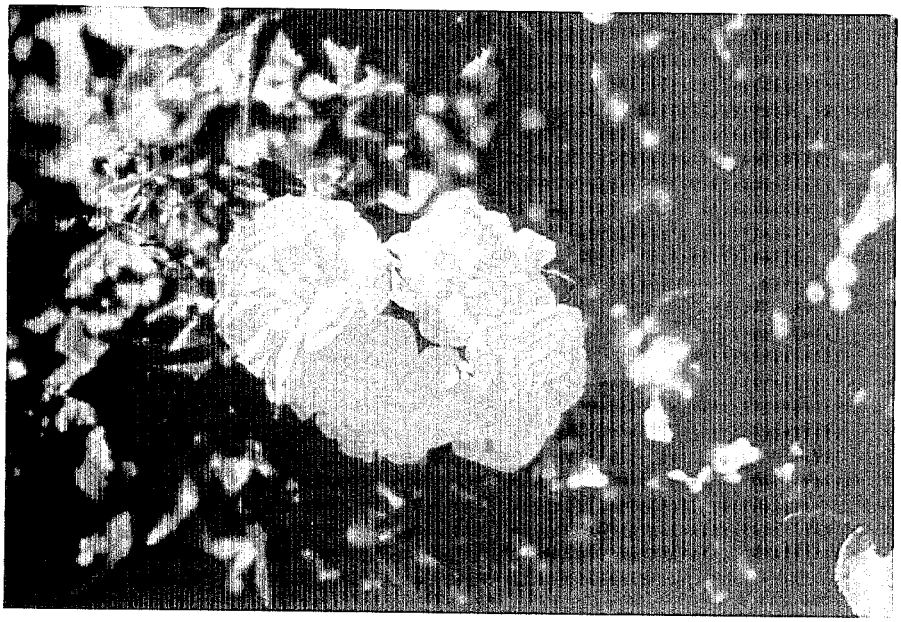
Figure 2:
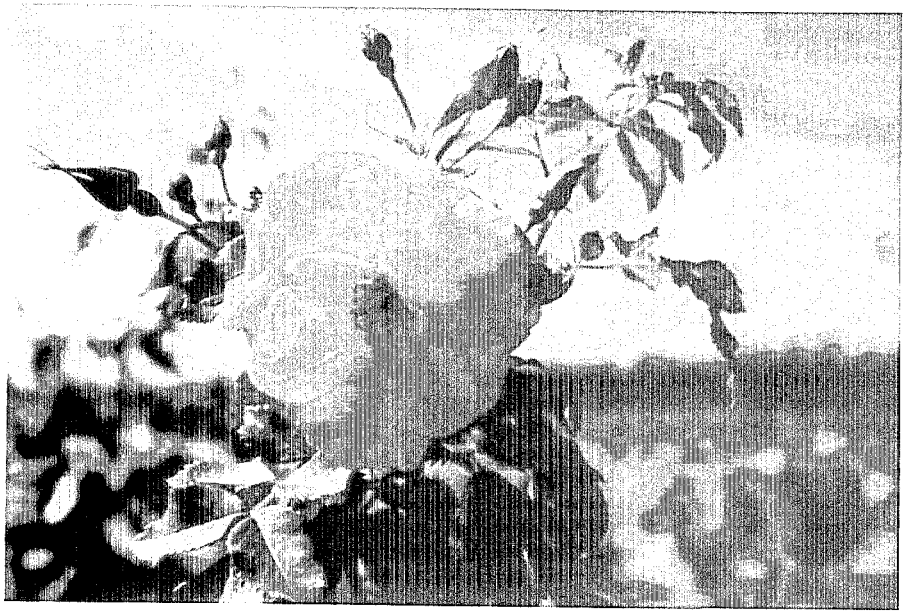
Figure 3:
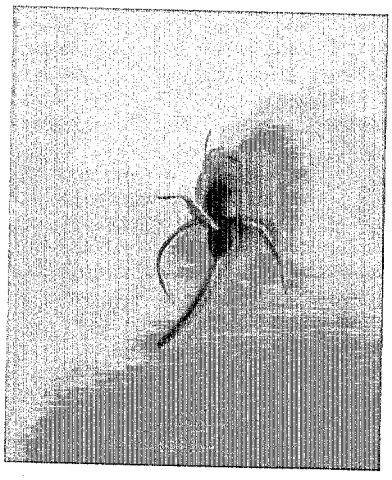
Figure 4:
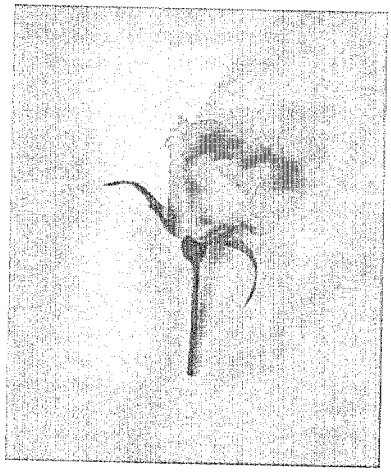
Figure 5:
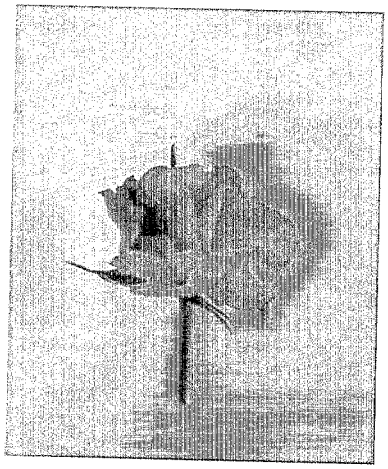
Figure 6:
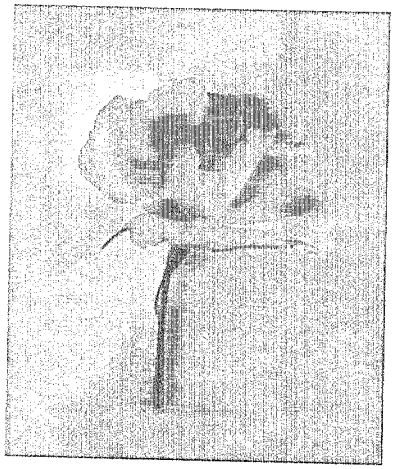
Figure 7:
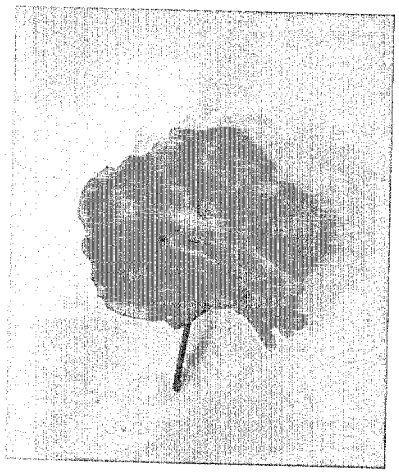
Figure 8:
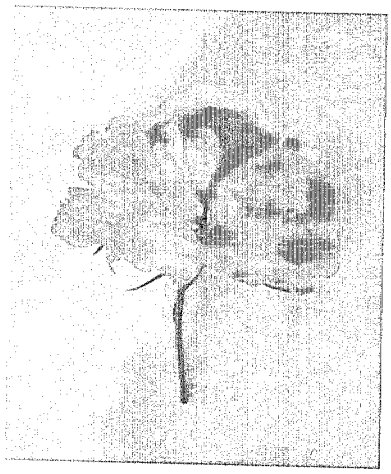
Figure 9:
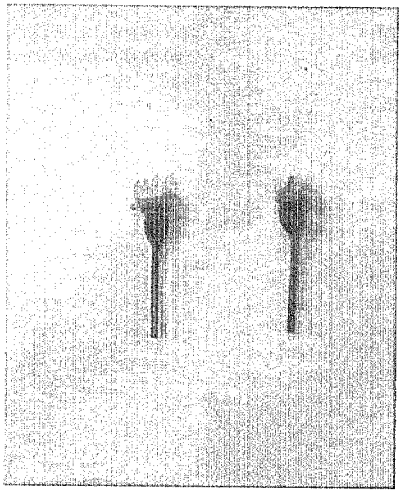
Figure 10:
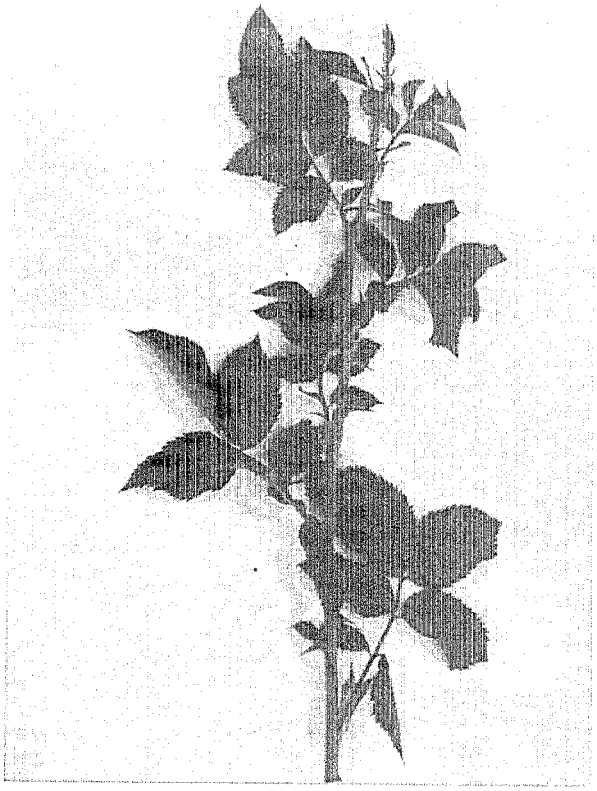
Figure 11:
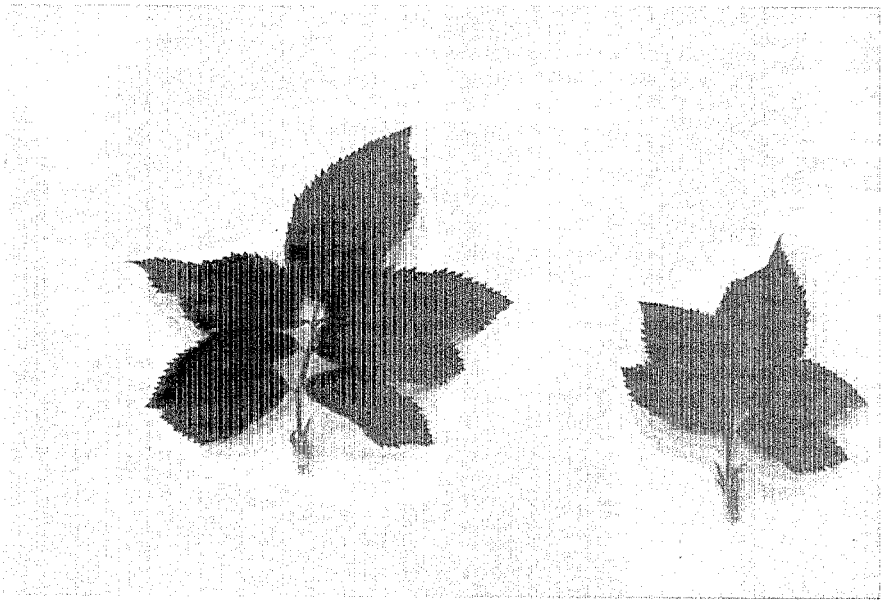
Figure 12:
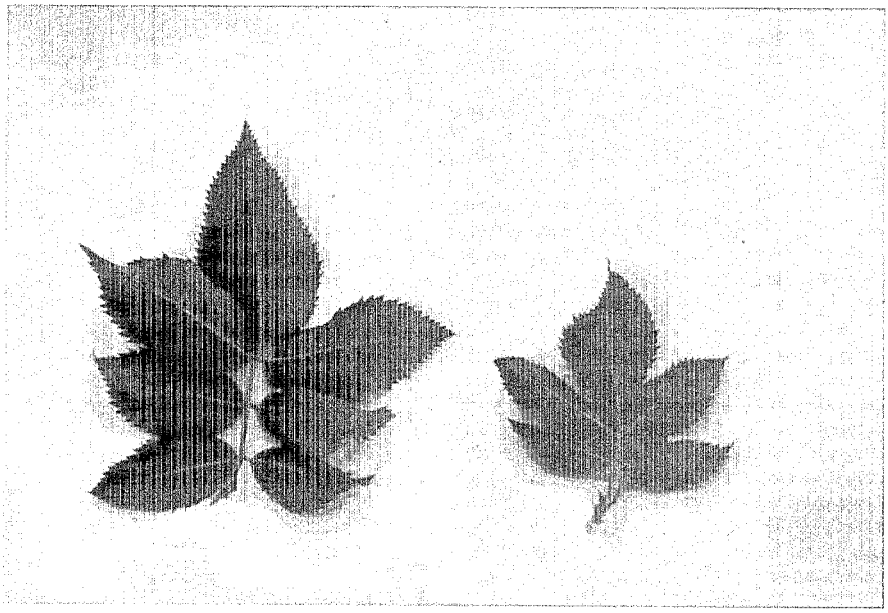

The chart used in the identification of colors is that of The Royal Horticultural Society (R.H.S. Colour Chart). Common color terms are to be accorded their ordinary dictionary significance. The description is based on the observation of 5 to 6 year-old plants of the new variety while being grown outdoors at L'Assomption, Quebec, Canada.

Class: Shrub.

Plant:

*Height.*—Approximately 1.5 to 1.8 meters on average.

*Width.*—Approximately 1 meter on average.

*Habit.*—Spreading and trailing.

Branches:

*Color.*—Young stems: medium green with a tinge of red. Mature stems: medium green.

*Prickles.*—Shape: slightly concave on the upper and under edges. Size: medium. Quantity: approximately 5 per 100 mm of stem on average.

*Color.*—Bright red when young and tan when mature.

Leaves: Compound and pinnate. stipules — narrow and linear with erect auricles.

*Petioles.*—Medium green with a tinge of red when young and yellowish green when mature.

*Petiolules.*—very short.

*Leaflets.*—Number: commonly 5 or 7. Shape: oval to rounded base, some are uneven, with acute tip. Serration: single and irregular.

*Color.*—Adult foliage: initially a light yellow green approximating Green Group 137C on the upper surfaces and darkens as the leaves mature (as illustrated). The under surfaces of the leaves commonly are lighter in coloration (as illustrated). General appearance: glossy.

*Rachis.*—Smooth with very small prickles on the underside.

Inflorescence:

*Number of flowers.*—Usually 1 to 10 per stem.

*Peduncle.*—Erect, medium green when young and when mature, slighty glandular commonly 3 to 3.5 cm. in length, commonly bears no prickles.

*Sepals.*—Commonly 5 in number, extend beyond the bud on young buds, commonly include foliation, medium green with a tinge of red when young and yellow green with a tinge of red when mature.

*Buds.*—Shape: pointed before the opening of the sepals, and progressively becoming ovoid upon opening. Color upon opening: the outer petals are deep pink.

*Flower.*—Shape: initially cup-shaped and subsequently assumes a flattened configuration (as illustrated). Diameter: approxiamtely 7 cm on average. Color (when blooming): deep fuchsia red, when young approaching Red-Purple Group 66B (but commonly with more red and less purple), on the upper surface, and lighter on the under surface, approaching Red-Purpple Group 66D. As the blossoms mature, the coloration lightens (as illustrated). Fragrance: slight. Petal number: approximately 23 on average. Petal texture: velvety. Lasting quality: the blossoms commonly last approximately 5 to 7 days while present on the plant under most growing conditions. Petals drop: the petals drop off fairly cleanly. Anthers: gold in coloration. Pollen: light yellow in coloration. Filaments: yellow-green in coloration. Receptacle: ovoid in configuration, green in coloration, and generally female sterile.

Development:

*Vegetation.*—Intermediate vigor.

*Blossoming.*—Flowers heavily during June and on a continuous basis but to a lesser degree throughout the remainder of the season.

*Hardiness.*—Survives consistently without cover in Eastern Canada (Zone 4, Quellet and Sherk, 1967).

*Resistance to diseases.*—Generally resistant to mildew and blackspot, some blackspot may be observed on the lower leaves at the end of the season.

*Preferred mode of propagation.*—The use of softwood cuttings to produce self-rooted plants in recommended for the production of quality cold-tolerant plants.

I claim:

1. A new and distinct variety of shrub rose plant characterized by the following combination of characteristics:

(a) exhibits a spreading and trailing growth habit with glossy foliage,
(b) forms on an intermediate basis in clusters attractive fuchsia red blossoms,
(c) propagates well by the use of sofwood cuttings,
(d) exhibits a good winter hardiness, and
(e) is particularly well suited for growing in the landscape;

substantially as herein shown and described.

* * * * *